United States Patent [19]
Eickhoff et al.

[11] Patent Number: 5,518,738
[45] Date of Patent: May 21, 1996

[54] NANOPARTICULATE NSAID COMPOSITIONS

[75] Inventors: W. Mark Eickhoff, Schwenksville; David A. Engers, Collegeville; Karl R. Mueller, Pexton, all of Pa.

[73] Assignee: NanoSystem L.L.C., Collegeville, Pa.

[21] Appl. No.: 385,614

[22] Filed: Feb. 9, 1995

[51] Int. Cl.⁶ .................................................. A61K 9/16
[52] U.S. Cl. ............................................................ 424/493
[58] Field of Search ............................ 514/570; 424/493

[56] References Cited

U.S. PATENT DOCUMENTS

| | | | |
|---|---|---|---|
| 5,145,684 | 9/1992 | Liversidge et al. | 424/489 |
| 5,183,829 | 2/1993 | Caldwell | 514/570 |

FOREIGN PATENT DOCUMENTS

| | | | |
|---|---|---|---|
| 0371431 | 11/1989 | European Pat. Off. | A61K 9/18 |
| WO90/1559 | 12/1990 | WIPO | A61K 9/10 |

OTHER PUBLICATIONS

Cioli et al., "Toxicological and Applied Pharmacology", 50, 283–289 (1979).

Price et al, "Drugs", 40 (Suppl. 5): 1–11, 1990.

*Primary Examiner*—Marianne M. Cintins
*Assistant Examiner*—Keith MacMillian
*Attorney, Agent, or Firm*—Rudman & Balogh

[57] ABSTRACT

A composition comprising a crystalline NSAID having polyvinylpyrrolidone adsorbed on the surface thereof in an amount sufficient to maintain an effective average particle size of less than about 1000 nm, hygroscopic sugar and sodium lauryl sulfate exhibit greatly reduced gastric irritation following oral administration and/or hastened onset of action due to the substantial redispersion of the solid formulation to nanoparticles in gastric fluid.

15 Claims, No Drawings

NANOPARTICULATE NSAID COMPOSITIONS

FIELD OF USE

This invention relates to pharmaceutical compositions containing NSAIDs used as analgesics for mammals.

BACKGROUND OF INVENTION

Nonsteroidal anti-inflammatory drugs (NSAIDs) are one of the most commonly used and therapeutically effective groups of drugs. However, gastric irritation problems constitute the most frequent recognized adverse side effect following oral administration of NSAIDs. Such side effects are well recognized and must be weighed against the clinical efficacy of the drugs.

A great amount of research has been undertaken in an attempt to understand the underlying mechanism responsible for these effects. For example, Cioli et al, *Tox, and Appl. Pharm.*, 50, 283-289 (1979) suggest that gastrointestinal lesions in laboratory animals resulting from the oral administration of acidic NSAIDs may depend on two different mechanisms: a local action exerted by contact with the gastric mucosa and a generalized/centrally mediated (systemic) action, taking place following oral administration.

More recently, Price et al, *Drugs* 40 (Suppl. 5):1–11, 1990, suggest that NSAID-induced gastric damage occurs as a result of NSAID-mediated direct and indirect acidic damage followed almost simultaneously by the deleterious systemic effect of prostaglandin inhibition.

A variety of strategies have been used in the management of NSAID-induced gastric damage. These include: 1) the development and use of NSAIDs with less toxic potential; 2) the reduction or elimination of the agent that actually causes the injury; and 3) the enhancement of the mucosal defense. However, these approaches have not proven entirely successful.

For example, the most effective means for preventing gastric damage, i.e., by eliminating the primary aetiological agent is rarely feasible with NSAIDs inasmuch as patients with severe inflammatory disease are rarely able to cease using these drugs. Although selection of less toxic NSAIDs should prove useful, the only practical solution, at present, is to treat the NSAID induced gastric damage. Misoprostol (a methylated prostaglandin $E_1$) has been approved by the FDA for use in preventing NSAID gastropathy. However, Misoprostol is expensive, must be administered multiple times daily and can cause unacceptable side effects.

In European Patent Application 89121865.3 filed Nov. 27, 1989, a process of milling drugs with salts is disclosed.

In PCT Application No. PCT/SE90/00426 filed Jun. 15, 1990, precipitated drug particles are described.

In copending U.S. Application Ser. No. 897,193 filed Jun. 10, 1992, the use of NSAID particles having a surface modifier adsorbed on the surface thereof in an amount sufficient to maintain an average particle size of less than about 1000 µm, was described as being useful in reducing gastric irritation in mammals.

It would be highly desirable to provide NSAID formulations that can exhibit a greater reduction in gastric irritation and exhibiting hastened onset of action as an analgesic.

SUMMARY OF THE INVENTION

It has been discovered that pharmaceutical compositions comprising NSAID nanoparticles having adsorbed on the surface thereof polyvinylpyrrolidone, in combination with hygroscopic sugar and sodium lauryl sulfate exhibits improved, reduced gastric irritation and/or more rapid onset of action as an analgesic in mammals and reduced absorption variability.

In accordance with this invention there are provided pharmaceutical compositions comprising particles consisting essentially of an NSAID having polyvinylpyrrolidone adsorbed on the surface thereof in an amount sufficient to maintain an average particle size of less than about 1000 nm, hygroscopic sugar and sodium lauryl sulfate.

This invention further provides a pharmaceutical composition comprising the above and a pharmaceutically acceptable carrier.

In another embodiment of this invention, there is provided a method of treating a mammal comprising administering to the mammal the above described pharmaceutical composition.

In further embodiments of the invention, there are provided methods of reducing gastric irritation and/or hastening the onset of action which include administering the above-described pharmaceutical composition to a mammal.

It is an advantageous feature of this invention that pharmaceutical compositions containing NSAIDs are provided which exhibit reduced gastric irritation following oral administration.

It is another advantageous feature of this invention that pharmaceutical compositions are provided exhibiting hastened onset of action.

Other advantageous features will become readily apparent upon reference to the following description of preferred embodiments.

DESCRIPTION OF PREFERRED EMBODIMENTS

This invention is based on the discovery that surface modified nanoparticles comprising an NSAID, e.g., naproxen, when combined with polyvinylpyrrolidone and combined with hygroscopic sugar and sodium lauryl sulfate demonstrate reduced gastric irritation and/or a more rapid onset of action following oral administration. While the invention is described herein primarily in connection with its preferred class of drugs, i.e., NSAIDs, it is also useful in conjunction with other classes of drug substances, e.g., antibiotics, quinolones, antilipemics and roentgenographics.

The particles of this invention comprise an NSAID. The NSAID exists as a discrete, crystalline phase. The crystalline phase differs from an amorphous or non-crystalline phase which results from conventional solvent precipitation techniques, such as described in U.S. Pat. No. 4,826,689. The NSAID can be present in one or more suitable crystalline phases.

The invention can be practiced with a wide variety of NSAIDs. However, the NSAID must be poorly soluble and dispersible in at least one liquid medium. By "poorly soluble" it is meant that the NSAID has a solubility in the liquid dispersion medium, e.g., water, of less than about 10 mg/ml, and preferably of less than about 1 mg/ml at processing temperature, e.g., room temperature. The preferred liquid dispersion medium is water. However, the invention can be practiced with other liquid media in which the NSAID is poorly soluble and dispersible including, for example, aqueous salt solutions, safflower oil and solvents such as ethanol, t-butanol, hexane and glycol. The pH of the aqueous dispersion media can be adjusted by techniques known in the art.

The NSAIDs useful in the practice of this invention can be selected from suitable acidic and nonacidic compounds. Suitable acidic compounds include carboxylic acids and enolic acids. Suitable nonacidic compounds include, for example, nabumetone, tiaramide, proquazone, bufexamac, flumizole, epirazole, inoridine, timegadine and dapsone.

Suitable carboxylic acid NSAIDs include, for example, salicylic acids and esters thereof, such as aspirin, diflunisal, benorylate and fosfosal; acetic acids, including phenylacetic acids such as diclofenac, alclofenac and fenclofenac, and carbo- and heterocyclic acetic acids such as etodolac, indomethacin, sulindac, rolmerin, fentiazac and tilomisole; propionic acids, such as carprofen, fenbufen, flurbiprofen, ketoprofen, oxaprozin, suprofen, triaprofenic acid, ibuprofen, naproxen, fenoprofen, indoprofen, piroprofen; and fenamic acids, such as flufenamic, mefenamic, meclofenamic and niflumic.

Suitable enolic acid NSAIDs include, for example, pyrazolones such as oxyphenbutazone, phenylbutazone, apazone and feprazone, and oxicams such as piroxicam, sudoxicam, isoxicam and tenoxicam.

The above-described NSAIDs are known compounds and can be prepared by techniques known in the art.

In particularly preferred embodiments of the invention, the NSAID is naproxen, ketoprofen, indomethacin or ibuprofen, and particularly naproxen.

The particles of this invention contain an NSAID as described above having a polyvinylpyrrolidone surface modifier adsorbed on the surface thereof.

The polyvinylpyrrolidone surface modifier is adsorbed on the surface of the NSAID in an amount sufficient to maintain an effective average particle size of less than about 1000 nm. The surface modifier does not chemically react with the NSAID or itself. Furthermore, the individually adsorbed molecules of the polyvinylpyrrolidone are essentially free of intermolecular crosslinkages.

By "hygroscopic sugar" is meant sugars wuch as sucrose, dextrose, mannose and lactose which absorb significant amounts of water, e.g., greater than 5% by weight at room temperature and high relative humidity, e.g. greater than 80% RH. The preferred hygroscopic sugar is sucrose.

As used herein, particle size refers to a number average particle size as measured by conventional particle size measuring techniques well known to those skilled in the art, such as sedimentation field flow fractionation, photon correlation spectroscopy, or disk centrifugation. By "an effective average particle size of less than about 1000 nm" it is meant that at least 90% of the particles have a number average particle size of less than about 1000 nm when measured by the above-noted techniques. In preferred embodiments of the invention, the effective average particle size is less than about 300 nm. With reference to the effective average particle size, it is preferred that at least 95% and, more preferably, at least 99% of the particles have a particle size of less than the effective average, e.g., 1000 nm. In particularly preferred embodiments, essentially all of the particles have a size less than 400 nm.

The particles of this invention can be prepared in a method comprising the steps of dispersing an NSAID in a liquid dispersion medium and applying mechanical means in the presence of grinding media to reduce the particle size of the NSAID to an effective average particle size of less than about 1000 nm. The particles can be reduced in size in the presence of the polyvinylpyrrolidone. Alternatively, the particles can be contacted with the polyvinylpyrrolidone after attrition.

A general procedure for preparing the particles of this invention is set forth below. The NSAID selected is obtained commercially and/or prepared by techniques known in the art in a conventional coarse form. It is preferred, but not essential, that the particle size of the coarse NSAID selected be less than about 100 μm, then it is preferred that the particles of the NSAID be reduced in size to less than 100 μm using a conventional milling method such as airjet or fragmentation milling.

The coarse NSAID selected can then be added to a liquid medium in which it is essentially insoluble to form a premix. The concentration of the NSAID in the liquid medium can vary from about 0.1–60%, and preferably is from 0–50% (w/w). It is preferred, but not essential, that the polyvinylpyrrolidone be present in the premix. The concentration of the polyvinylpyrrolidone can vary from about 0.1 to about 90%, and preferably is 1–75%, more preferably 5–20%, by weight based on the total combined weight of the drug substance and polyvinylpyrrolidone. The apparent viscosity of the premix suspension is preferably less than about 1000 centipoise.

The premix can be used directly by subjecting it to mechanical means to reduce the average particle size in the dispersion to less than 1000 nm. It is preferred that the premix be used directly when a ball mill is used for attrition. Alternatively, the NSAID and, optionally, the surface modifier, can be dispersed in the liquid medium using suitable agitation, e.g., a roller mill or a Cowles type mixer, until a homogeneous dispersion is observed in which there are no large agglomerates visible to the naked eye. It is preferred that the premix be subjected to such a premilling dispersion step when a recirculating media mill is used for attrition.

The mechanical means applied to reduce the particle size of the NSAID conveniently can take the form of a dispersion mill. Suitable dispersion mills include a ball mill, an attritor mill, a vibratory mill, a planetary mill, media mills such as a sand mill and a bead mill. A media mill is preferred due to the relatively shorter milling time required to provide the intended result, i.e., the desired reduction in particle size. For media milling, the apparent viscosity of the premix preferably is from about 100 to about 1000 centipoise. For ball milling, the apparent viscosity of the premix preferably is from about 1 up to about 100 centipoise. Such ranges tend to afford an optimal balance between efficient particle fragmentation and media erosion.

The grinding media for the particle size reduction step can be selected from rigid media preferably spherical or particulate in form having an average size less than about 3 mm and, more preferably, less than about 1 mm. Such media desirably can provide the particles of the invention with shorter processing times and impart less wear to the milling equipment. The selection of material for the grinding media is not believed to be critical. However, polymeric grinding media and zirconium oxide, such as 95% ZrO stabilized with magnesia, zirconium silicate, and glass grinding media provide particles having levels of contamination which are believed to be acceptable for the preparation of pharmaceutical compositions. Further, other media, such as stainless steel, titania, aluminia, and 95% ZrO stabilized with yttrium, are expected to be useful.

The attrition time can vary widely and depends primarily upon the particular mechanical means and processing conditions selected. For ball mills, processing times of up to five days or longer may be required. On the other hand, processing times of less than 1 day (residence times of one minute up to several hours) have provided the desired results using a high shear media mill.

The particles must be reduced in size at a temperature which does not significantly degrade the NSAID. Processing temperatures of less than about 30°– 40° C. are ordinarily preferred. If desired, the processing equipment can be cooled with conventional cooling equipment. The method is conveniently carried out under conditions of ambient temperature and at processing pressures which are safe and effective for the milling process. For example, ambient processing pressures are typical of ball mills, attritor mills and vibratory mills. Processing pressures up to about 20 psi (1.4 kg/cm$^2$) are typical of media milling.

Milling must be carried out under acidic conditions, at a pH of from 2–6, preferably 3–5. The preferred pH depends, e.g., on the acidity and solubility of the particular NSAID selected. Acid resistant milling equipment is highly preferred, e.g., equipment fabricated of high grade stainless steel, e.g., grade 316 SS, or equipment coated with an acid resistant coating.

The polyvinylpyrrolidone, if it was not present in the premix, must be added to the dispersion after attrition in an amount as described for the premix above. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

The relative amount of the NSAID and polyvinylpyrrolidone can vary widely and the optimal amount of the polyvinylpyrrolidone can depend, for example, upon the critical micelle concentration of the polyvinylpyrrolidone if it forms micelles, the surface area of the NSAID, etc. The polyvinylpyrrolidone preferably is present in an amount of about 0.1–10 mg per square meter surface area of the NSAID. The polyvinylpyrrolidone can be present in an amount of 0.1–90%, preferably 0.5–80%, and more preferably 1–60% by weight based on the total weight of the dry particle.

The polyvinylpyrrolidone coated NSAID is mixed with hygroscopic sugar and sodium lauryl sulfate in an acceptable medium and as water.

In order to obtain a more uniform film, a film former such as mannitol can be added to the polyvinylpyrrolidone, hygroscopic sugar and sodium lauryl sulfate. Mannitol is a preferred film former.

The pharmaceutical composition comprises from 10 to 75 % by weight of hygroscopic sugar, preferably 25% and from 0.1 to 10% by weight of sodium lauryl sulfate, preferably 3% and 1 to 50% of weight of a film former, preferably 10–15%.

Pharmaceutical compositions according to this invention can include the composition described above and a pharmaceutically acceptable carrier therefor. Suitable pharmaceutically acceptable carriers are well known to those skilled in the art. These include non-toxic physiologically acceptable carriers, adjuvants or vehicles for parenteral injection, for oral administration in solid or liquid form, for rectal administration, and the like. A method of treating a mammal in accordance with this invention comprises the step of administering to the mammal in need of treatment the effective amount of the above-described pharmaceutical composition. The selected dosage level of the NSAID for treatment is effective to obtain a desired therapeutic response for a particular composition and method of administration. The selected dosage level therefore, depends upon the particular NSAID, the desired therapeutic effect, on the route of administration, on the desired duration of treatment and other factors.

It is a particularly advantageous feature that the pharmaceutical compositions of this invention exhibit reduced gastric irritation and/or more rapid onset of action as illustrated in the example that follow.

The following example further illustrate the invention.

EXAMPLE I

The following solid films were prepared from a stock nanoparticulate dispersion that was 40 wt % naproxen: 2.5 wt % PVP (K29/32) in water. Redispersants were added to the dispersion and dried in the oven to produce solid films. The films were redispersed in SGF (simulated gastric fluid) at 37° C. for 20 minutes and centrifuged to remove agglomerates. The supernatant containing the nanoparticulates was assayed and particle sized for comparison to the stock dispersion which was also diluted in SGF and centrifuged but not dried.

| Redispersant (%)* | wt % supernatant** | PS supernatant*** |
|---|---|---|
| hygroscopic sugar (37) | 10 | nd |
| SLS (6) | 38 | nd |
| hygroscopic sugar + SLS (31 + 6) | 84 | 404–543 nm |
| DOSS (6) | 0.5 | nd |
| benzalkonium chloride(6) | 15 | nd |
| stock dispersion (SGF) | na | 446–572 nm |
| stock dispersion (water) | na | 400–480 nm |

*based on wt of naproxen
**based on concentration of naproxen in supernatant of stock dispersion diluted in SGF 1:10
***mean particle size by Microtrek UPA (50%-mv); n = 2
na not applicable
nd not determined It is thus seen that the use of hygroscopic sugar and sodium lauryl sulfate as a combination of redispersants for the NSAID nanoparticles act synergistically in that addition of hygroscopic sugar or sodium lauryl sulfate alone is not sufficient to redisperse the solid nanonaproxen in gastric fluid to a great extent. The redispersibility of this novel composition enhances its utility as it reduces gastric irritation and hastens onset of analgesic activity of the NSAID.

Preparation 1

To 575 g of deionized water was dissolved 25 g of polyvinylpyrrolidone (K29/32; BASF Corpl) using a continuous laboratory mixer. 400 g of naproxen was dispersed into the PVP solution until a homogenous suspension was obtained. It was processed through a laboratory scale media mill filled with polymeric grinding media in a continuous fashion until the mean particle size was approximately 200 nm as measured by laser light scattering technique, ex. MicroTrak UPA. The 40% naproxen dispersion was collected and added to dissolve 180 g of sucrose, 80 g of mannitol, and 24 g of sodium lauryl sulfate using a laboratory mixer.

EXAMPLE 2

The final dispersion prepared in preparation 1 was dried in a tray oven at 60° C. to a hard film and allowed to equilibrate at room temperature for 2 days. The film was ground to a fine powder using a mortar and pestle. It was hand-filled into gelatin capsules (size 00) to a strength of 250 mg naproxen/capsule.

Alternatively, the dispersion may be sprayed dried to a fine powder using a laboratory spray drier or directly spray coated onto non-pareil seeds in a fluidized bed coater.

| Bioavailability Results in Fed Dogs | | |
| --- | --- | --- |
| Formulation | Dose* | MAT** |
| Preparation 1 | 250 | 12 |
| Example 2 | 250 | 14 |
| Anaprox Caplet (Syntex) | 250 | 45 |
| Naprosyn Suspension (Syntex) | 250 | 49 |

*mg of naproxen per dog (free acid basis)
**MAT = mean-absorption-time in minutes (n = 4–9)

We claim:

1. A solid dosage form pharmaceutical composition comprised of particles having an average particle size of less than about 1000 nm, wherein the particles consist essentially of an NSAID having a film adsorbed on the surface, the film consisting essentially of polyvinylpyrrolidone, hydroscopic sugar and sodium lauryl sulfate.

2. The composition of claim 1 wherein the average particle size is less than 400 μm.

3. The composition of claim 1 wherein polyvinylpyrrolidone is present in an amount of 0.1 to 90% by weight based on the total weight of the drug nanoparticle.

4. The composition of claim 1 wherein said NSAID is selected from nabumetone, tiaramide, proquazone, bufexamac, flumizole, epirazole, tinoridine, timegadine, dapsone, aspirin, diflunisal, benorylate, fosfosal, diclofenac, alclofenac, fenclofenac, etodolac, indomethacin, sulindac, tometin, fentiazac, tilomisole, carprofen, fenbufen, flurbiprofen, ketoprofen, oxaprozin, suprofen, tiaprofenic acid, ibuprofen, naproxen, fenoprofen, indoprofen, pirprofen, flufenamic, mefenamic, meclofenamic, niflumic, oxyphenbutazone, phenylbutazone, apazone and feprazone, piroxicam, sudoxicam, isoxicam and tenoxicam.

5. The composition of claim 1 wherein said NSAID is selected from naproxen, ketoprofen, indomethacin and ibuprofen.

6. The composition of claim 5 wherein said NSAID is naproxen.

7. The composition of claim 1 wherein the hygroscopic sugar is sucrose.

8. The composition of claim 1 comprising from 10 to 75% by weight of hygroscopic sugar.

9. The composition of claim 1 comprising from 0.1 to 10% by weight of sodium lauryl sulfate.

10. The composition of claim 1 further comprising a pharmaceutically acceptable carrier.

11. A method of treating a mammal comprising administering to the mammal an effective amount of the pharmaceutical composition of claim 10.

12. A method of reducing gastric irritation following oral administration to a mammal of the pharmaceutical composition of claim 10.

13. A method of hastening onset of action following administration to a mammal of the pharmaceutical composition of claim 1.

14. A method of reducing absorption variability following administration to a mammal of the pharmaceutical composition of claim 1.

15. A solid dosage form pharmaceutical composition comprised of particles having an average particle size of less than about 1000 nm, wherein the particles consist essentially of naproxen having a film adsorbed on the surface thereof, the film consisting essentially of 0.1 to 90% by weight, based on the weight of naproxen, of polyvinylpyrrolidone; 0.1 to 75% by weight of sucrose; 0.1 to 10% by weight of sodium lauryl sulfate; and 1 to 50% by weight of a film former.

* * * * *